United States Patent
Crison et al.

(10) Patent No.: US 6,207,191 B1
(45) Date of Patent: *Mar. 27, 2001

(54) MULTI-STAGE DRUG DELIVERY SYSTEM

(75) Inventors: John R. Crison; Gordon L. Amidon, both of Ann Arbor, MI (US)

(73) Assignee: Port Systems, L.L.C., Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/372,913

(22) Filed: Aug. 12, 1999

Related U.S. Application Data

(63) Continuation of application No. 08/946,515, filed on Oct. 7, 1997, now Pat. No. 5,976,571, which is a continuation-in-part of application No. 08/383,830, filed on Feb. 6, 1995, now Pat. No. 5,674,530, which is a division of application No. 08/251,731, filed on May 31, 1994, now Pat. No. 5,387,421, which is a continuation of application No. 07/826,253, filed on Jan. 27, 1992, now abandoned, which is a continuation of application No. 07/648,968, filed on Jan. 31, 1991, now abandoned.

(51) Int. Cl.[7] .................................................. A61K 9/22
(52) U.S. Cl. ..................... 424/472; 424/453; 424/464; 424/466; 424/468; 424/470
(58) Field of Search ................................. 424/472, 453, 424/464, 466, 468, 470

(56) References Cited

U.S. PATENT DOCUMENTS 4,773,907 * 9/1988 Urguhart et al. .
4,777,049 * 10/1988 Magruder et al. .

* cited by examiner

*Primary Examiner*—Raj Bawa
(74) *Attorney, Agent, or Firm*—Hudak & Shunk Co. LPA

(57) ABSTRACT

A drug delivery system (10) includes a first capsule half (12) having an inner chamber (16) containing a drug (18) therein. A plug (28) is disposed in a passageway (26) of the capsule half (12) for plugging the opening (24) thereof. The plug (28) is releasable from the passageway opening (24) upon the application of pressure from within the inner chamber (16). A pump mechanism, reactive with the external environment of the capsule half (12), causes an increase in pressure within the inner chamber (16) and forces the plug (28) out of the passageway (26) to release the drug (18) from the inner chamber (16) and out of the passageway (26). Thusly, after initial release of drug from a second capsule half (14) releasably mounted on the first capsule half (12), the first capsule half (12) provides a second pulse of drug release at a predetermined time after initial ingestion of the capsule. The invention further provides a method of manufacturing the drug delivery system (10) and method by which the drug delivery system (10) provides the drug to a body.

20 Claims, 7 Drawing Sheets

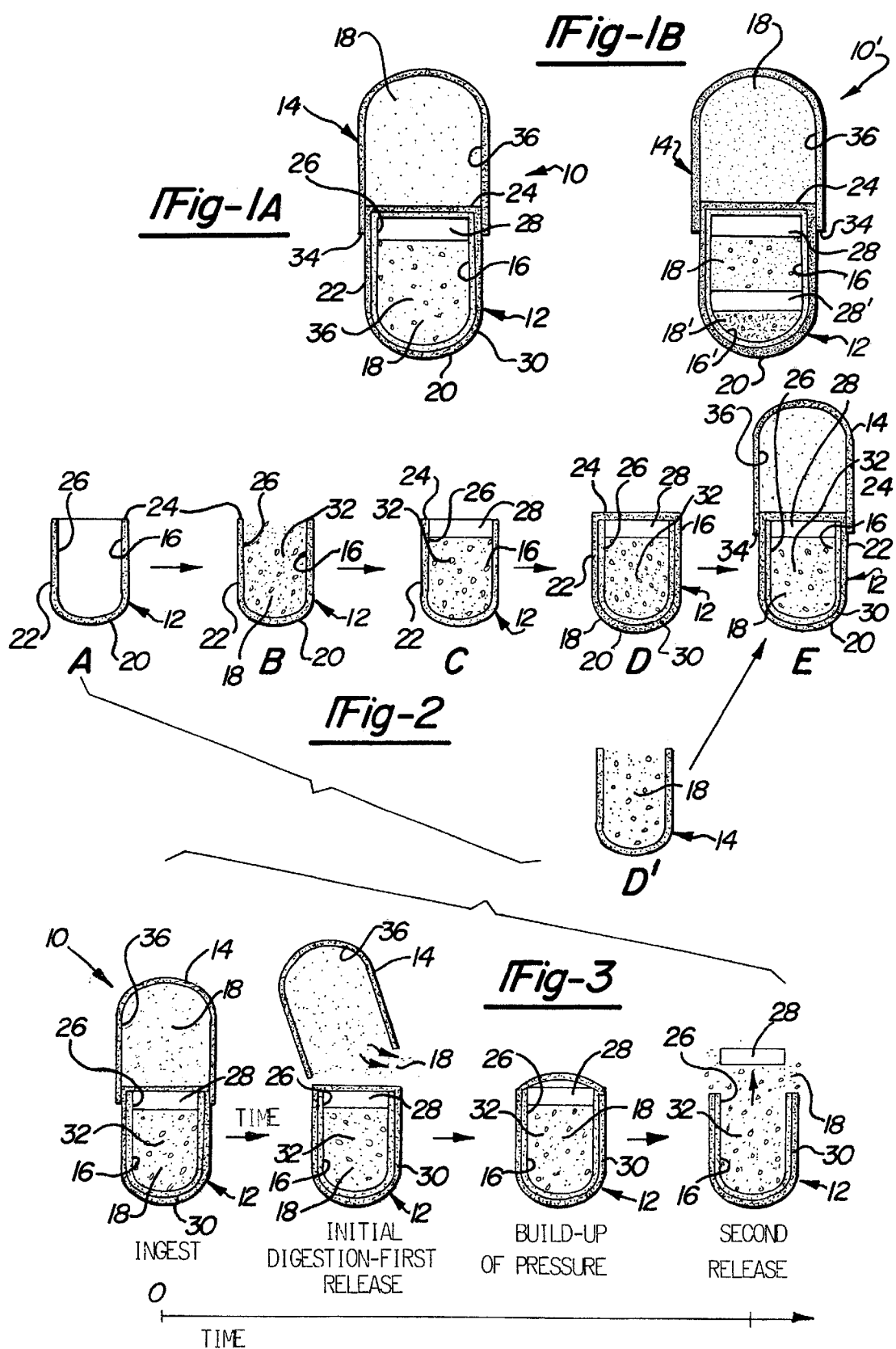

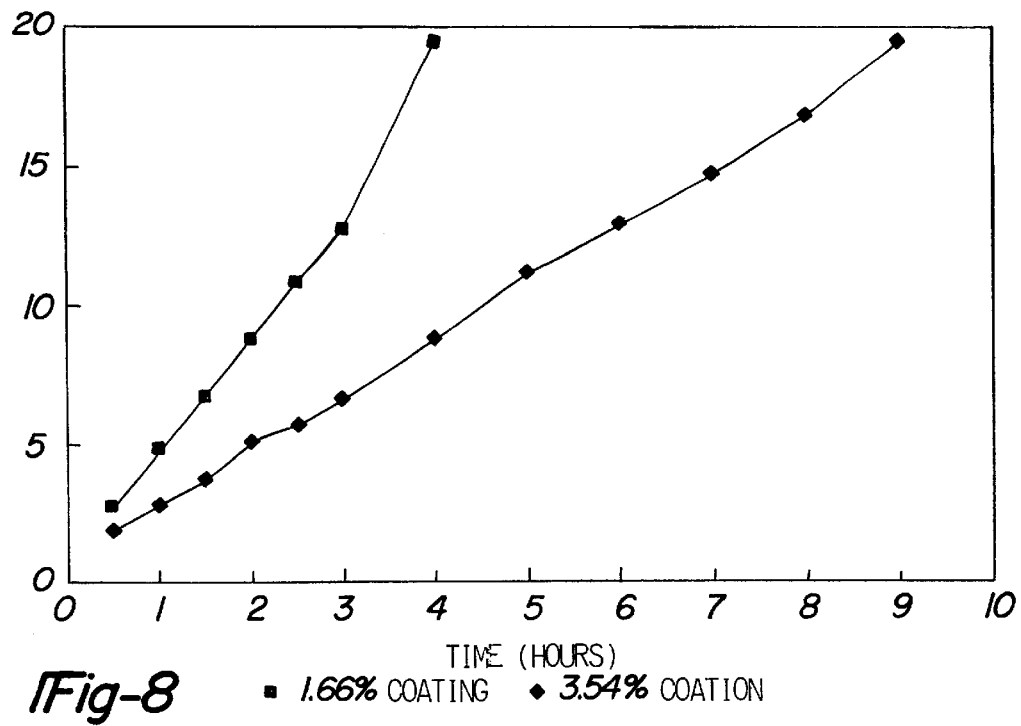
Fig-8  ■ 1.66% COATING  ◆ 3.54% COATION
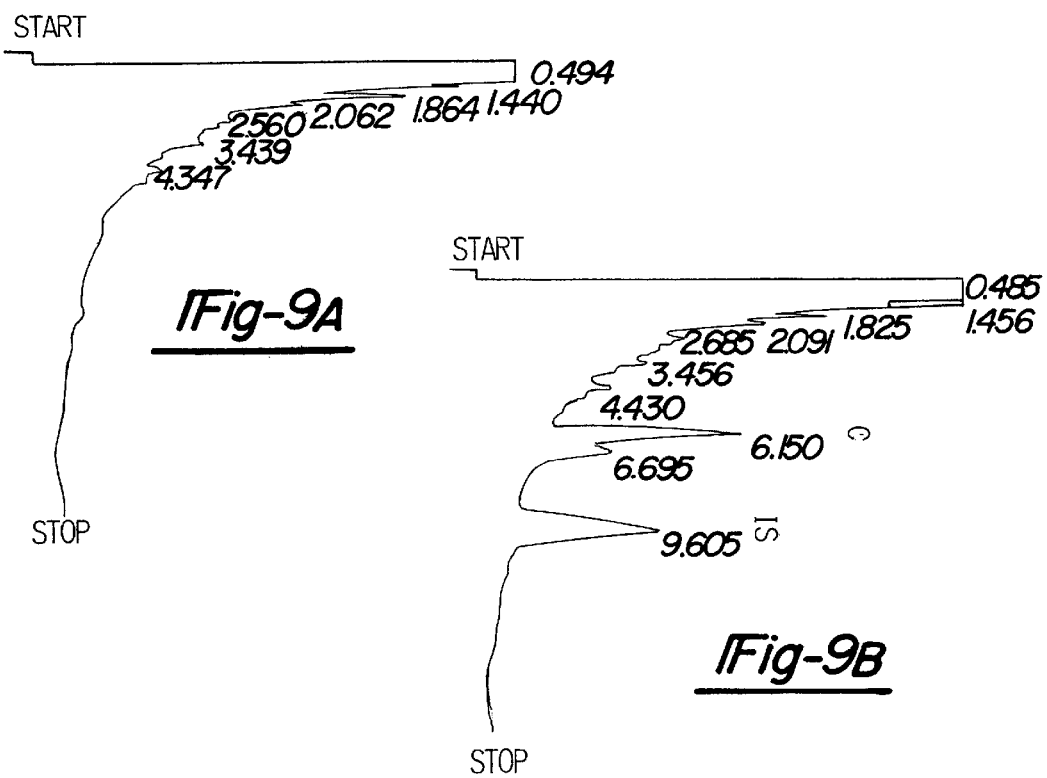
Fig-9A
Fig-9B

MULTI-STAGE DRUG DELIVERY SYSTEM

CROSS-REFERENCE

This is a continuation of applcation Ser. No. 08/946,515, filed on Oct. 7, 1997, of John R. Crison and Gordon L. Amidon METHOD FOR MAKING A MULTI-STAGE DRUG DELIVERY SYSTEM now U.S. Pat. No. 5,976,571 which in turn is a continuation-in-part application of Ser. No. 08/383,830, filed on Feb. 6, 1995, for. METHOD FOR MAKING A MULTI-STAGE DRUG DELIVERY SYSTEM, now U.S. Pat. No. 5,674,530, issued Oct. 7, 1997 which in turn is a divisional of Ser. No. 08/251,731, filed May 31, 1994, for METHOD FOR MAKING A MULTI-STAGE DRUG DELIVERY SYSTEM, now U.S. Pat. No. 5,387,421, issued Feb. 7, 1995 which in turn is a continuation of Ser. No. 07/826,253, filed Jan. 27, 1992 for METHOD FOR MAKING A MULTI-STAGE DRUG DELIVERY SYSTEM, abandoned, which in turn is a continuation of Ser. No. 07/648,968, Jan. 31, 1991 for METHOD FOR MAKING A MULTI-STAGE DRUG DELIVERY SYSTEM, abandoned.

TECHNICAL FIELD

This invention relates generally to drug delivery systems.

BACKGROUND OF THE INVENTION

It has been recognized that there is a need for a drug delivery system which yields an increase in the oral dosing interval of drugs exhibiting presystemic loss metabolism while simultaneously maintaining bioavailability equivalent to the immediate release dosage form. Such drugs would otherwise either require short interval dosing, such as periodic oral dosing having short periods between each oral dosing.

Various drug delivery systems, commonly referred to as time released systems, have attempted to solve this problem by continuously releasing amounts of the drug throughout the travel of the drug through the digestive track. For example, the U.S. Pat. No. 4,773,907 to Urquhart et al, issued Sep. 27, 1988, discloses a delivery system comprising a capsule containing dosage forms comprising a semipermeable wall surrounding a compartment containing drug. A passageway through the semipermeable wall releases drug from the dosage form to the environment. The U.S. Pat. No. 4,777,049 to Magruder et al, issued Oct. 11, 1988, discloses an osmotic delivery system. The system provides a device including a wall which can be a laminate comprising a semipermeable lamina and lamina arrangement with a microporous lamina. The lamina provides micropaths for emitting external fluid into the osmotic device. The device includes an opening having an erodible element, such as a gelatin plug that erodes and forms an osmotic passageway in the environment of use. Within the device is a modulating agent in nonequilibrium proportions. Upon the influx of fluid into the device, there is co-solubilization of a useful agent which is then released from the device. Thusly, co-solubilization of a modulating agent and a useful agent controls the release of the useful agent and results in the delayed release of the useful agent resulting from a reduction of the concentration of the modulating agent. This results in an osmotic system and a method of preprogramming to a desired time of release, a delayed release or a delayed pulsed release of agent. However, the delayed pulse of release is over a base line release and not a true pulse release from a zero base line.

The U.S. Pat. No. 4,783,337 to Wong et al, issued Nov. 8, 1988, discloses an osmotic system comprising a wall which is at least in part a semipermeable material that surrounds a compartment. An osmotic composition, or several osmotic compositions are contained within the compartment defined by the wall and a passageway in the wall connects the first composition with the exterior of the system. The first composition causes imbibition of fluid which results in the delivery of the suspension or solution through the aforementioned passageway. This can end up being a multi-chamber device.

European Patent 384 642 to Rashid, issued Dec. 15, 1993, discloses a water permeable capsule formed from at least two separable pieces and preferably uses a water swellable material to separate the two pieces and release the active material. The device disclosed in this application includes both a fluid permeable plug and fluid permeable capsule having water sensitive material disposed therebetween. In this configuration, the plug is forced out of the capsule by fluid ingressing through both the plug and the capsule wall to cause the water swellable material to physically increase in size and force the plug from the capsule. However, if this device were to include an osmotic reagent for generating osmotic pressure to force the plug from the capsule, the device would be inoperable as the permeability of both the capsule wall and plug would allow the escape or leakage of internal pressure which would prevent the build-up of adequate internal pressure and would not separate the plug from the capsule.

The aforementioned patents do not result in a truly pulsatile release. Pulsatile release, as used herein, implies an initial first release followed by a period of time where there is absolutely no release. Then, after the predetermined period, there is a true pulse release. Unlike prior art systems, it is desirable to provide a drug delivery system for non-linear presystemic loss drugs which will release fractions of the total dose at specified sites and time in the gastro-intestinal track so that bioavailability will not be compromised by the decreased release rate of conventionally controlled or sustained release dosage forms.

There are several advantages to a true pulsatile delivery system in extending the dosing interval. For those drugs which are first pass metabolized, an increase in delivery rate to the portal system results in a decrease in metabolism. For those drugs exhibiting non-linear prehepatic metabolism a larger fraction of drug will escape metabolism and therefore be available. For those drugs with incomplete absorption due to low permeability, poor solubility or in which case the absorption rate limited by rate of dissolution, enhancers can be added to increase the bioavailability. The pulse time and release rate can be programmed to match the immediate release dosage form profile. The pulse time and release rate from pulsatile delivery can be more reproducible than the immediate release dosage form which relies on patient compliance and rate of gastric emptying for input of drug to the site of absorption, that being the small intestine. The result is a decreased variability in plasma level time curves. The clinical efficacy of a pulsatile delivery system can be established to provide equivalent bioavailability to the conventional dosage form. Accordingly, patient compliance is increased through the use of a reduced and/or simpler dosing schedule. The pharmacodynamics of the pulsatile system can be made to match the established immediate release dosage. Thereby, the metabolic rates equivalent to that obtained from an approved dosing schedule can be obtained, hence no unusual accumulation of metabolites or altered metabolic profile results. The pulse delay and amount being pulsed are programmable to a variety of dosing schedules such that allowance for circadian rhythms is possible in order to optimize the pharmacodynamic response throughout the day. Finally, the optimal dosing schedule for two or more drugs, tailored to their individual pharmacokinetic and pharmacodynamic properties, can be optimized using this technology. The present invention provides an improved means of providing a pulsed dose or doses which are capable of providing all of the aforementioned advantages.

SUMMARY OF THE INVENTION

In accordance with the present invention, there is provided a drug delivery system comprising a first container including an inner chamber for containing a drug therein and having a passageway opening to an external environment thereof. Plug means is disposed in the passageway for plugging and closing the opening. The plug means is releasable from the opening upon the application of pressure from within the inner chamber. The container includes pump means reactive to the external environment for increasing the pressure within the inner chamber and forcing the plug means out of the passageway to release the drug from the chamber and out of the passageway.

The present invention further provides a method of delivering a drug to a body, the method including the steps of ingesting a drug delivery system, immediately releasing a first predetermined amount of drug from a second chamber of the system, and increasing the pressure within a first chamber of the system over time and forcing a plug therefrom at a predetermined time after the ingesting step. The drug is released from the first chamber once the plug is released therefrom.

The present invention further provides a method of making a drug delivery system, the method including the steps of filling a first capsule half with drug and a reactive agent, the capsule being water permeable. The capsule is plugged and a water permeable film is disposed over the capsule and plug. A second capsule half is filled with drug and an open end thereof is releasably mounted over the plugged end of the first capsule half.

Also, in accordance with the present invention, there is provided a method of making a drug delivery system includes the steps of filling a first capsule half with a drug and an osmotic agent, the capsule being water permeable. The method further includes the step of plugging an open-end of the capsule, disposing a water permeable film over the capsule and plug, filling a second capsule half with a drug, and releasably mounting an open end of the second capsule half over the plugged end of the first capsule half.

FIGURES IN THE DRAWINGS

Other advantages of the present invention will be readily appreciated as the same becomes better understood by reference to the following detailed description when considered in connection with the accompanying drawings wherein:

FIG. 1A is cross sectional view of a drug delivery system made in accordance with the present invention;

FIG. 1B is a cross sectional view of a multi-chamber drug delivery system made in accordance with the present invention;

FIG. 2 shows the steps of manufacturing the drug delivery system of the present invention;

Figure 4:
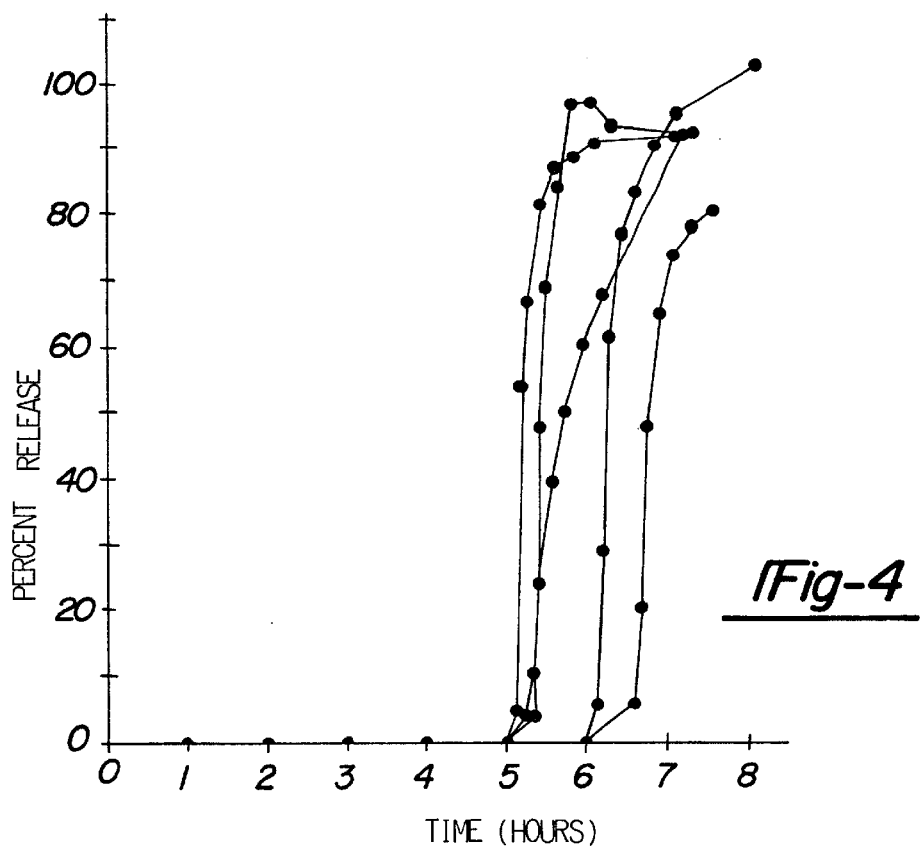
Figure 5:
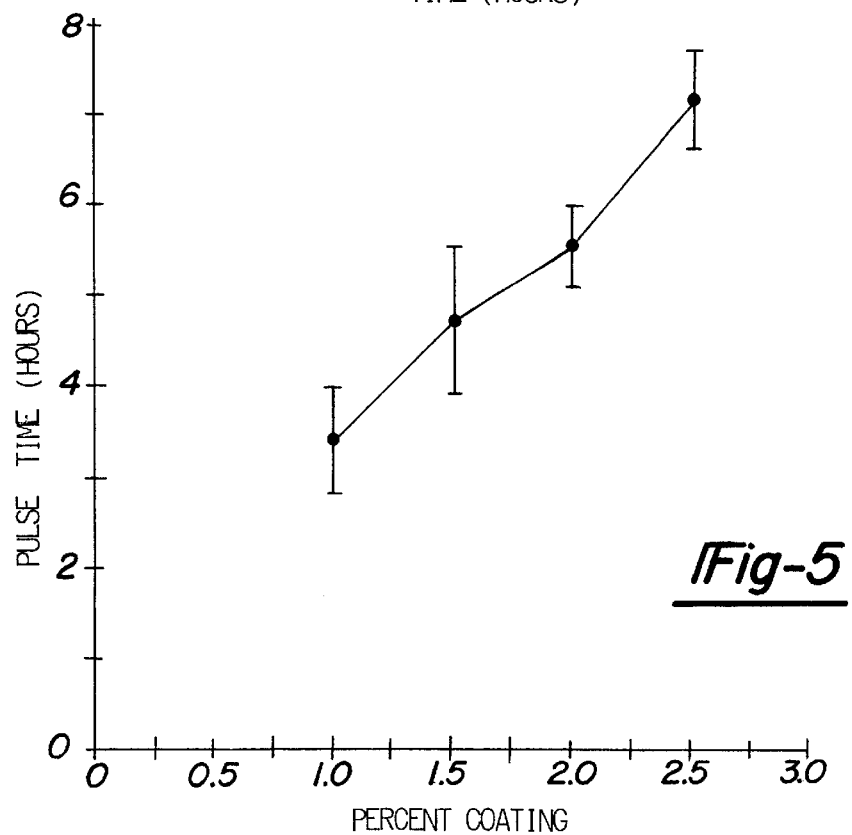
Figure 6:
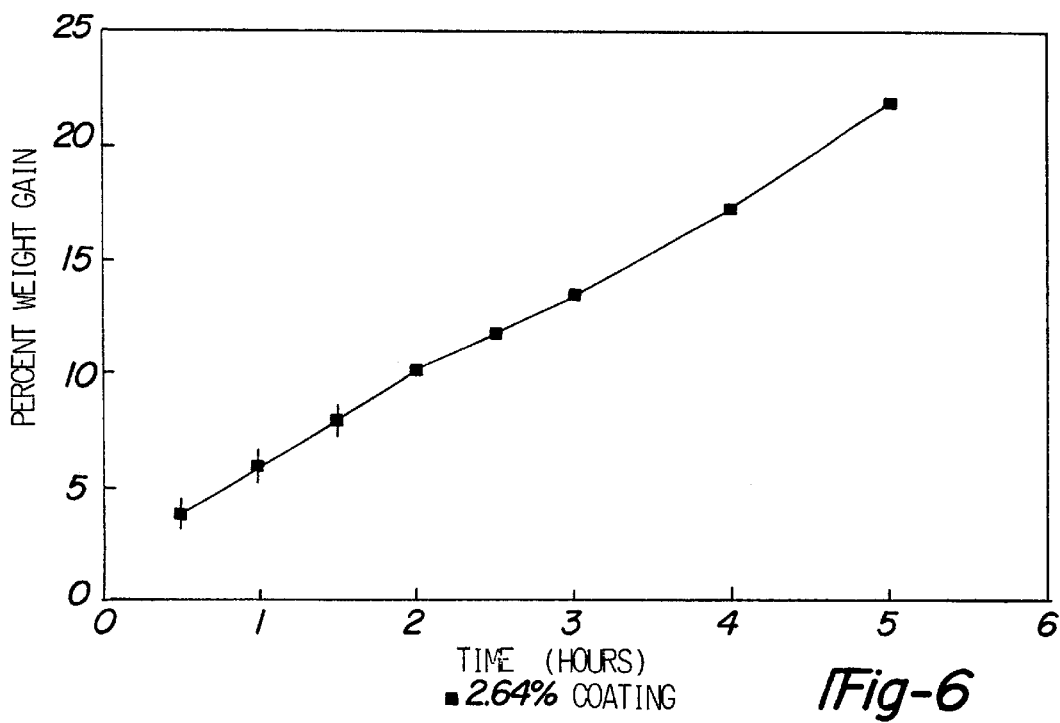
Figure 7:
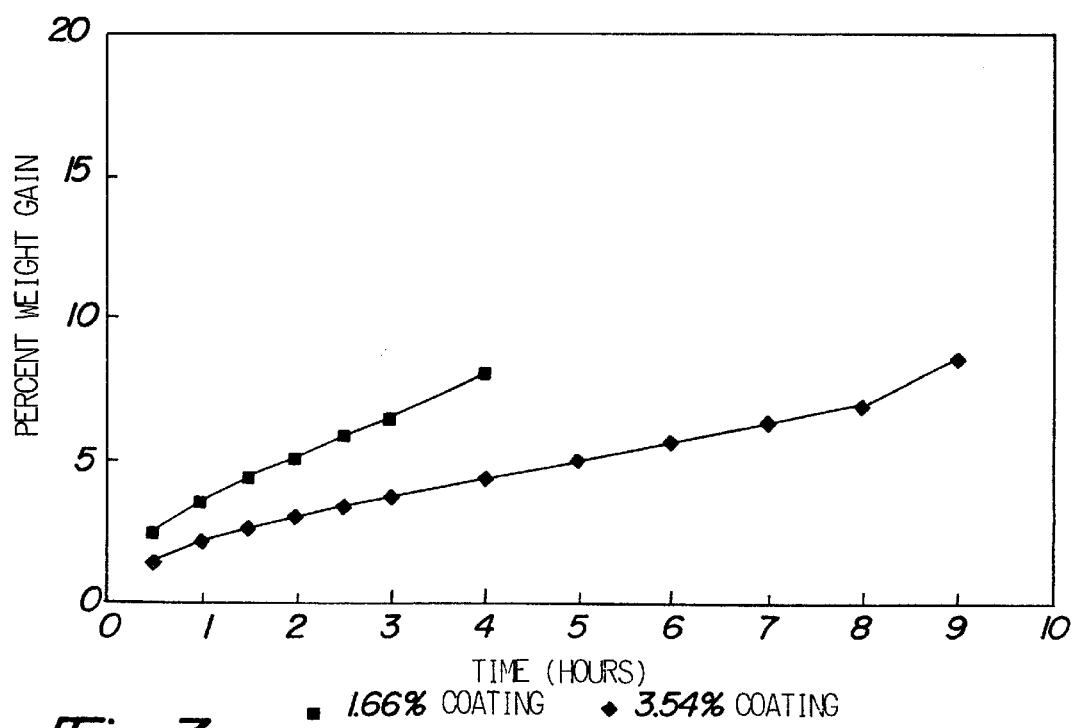
Figure 10:
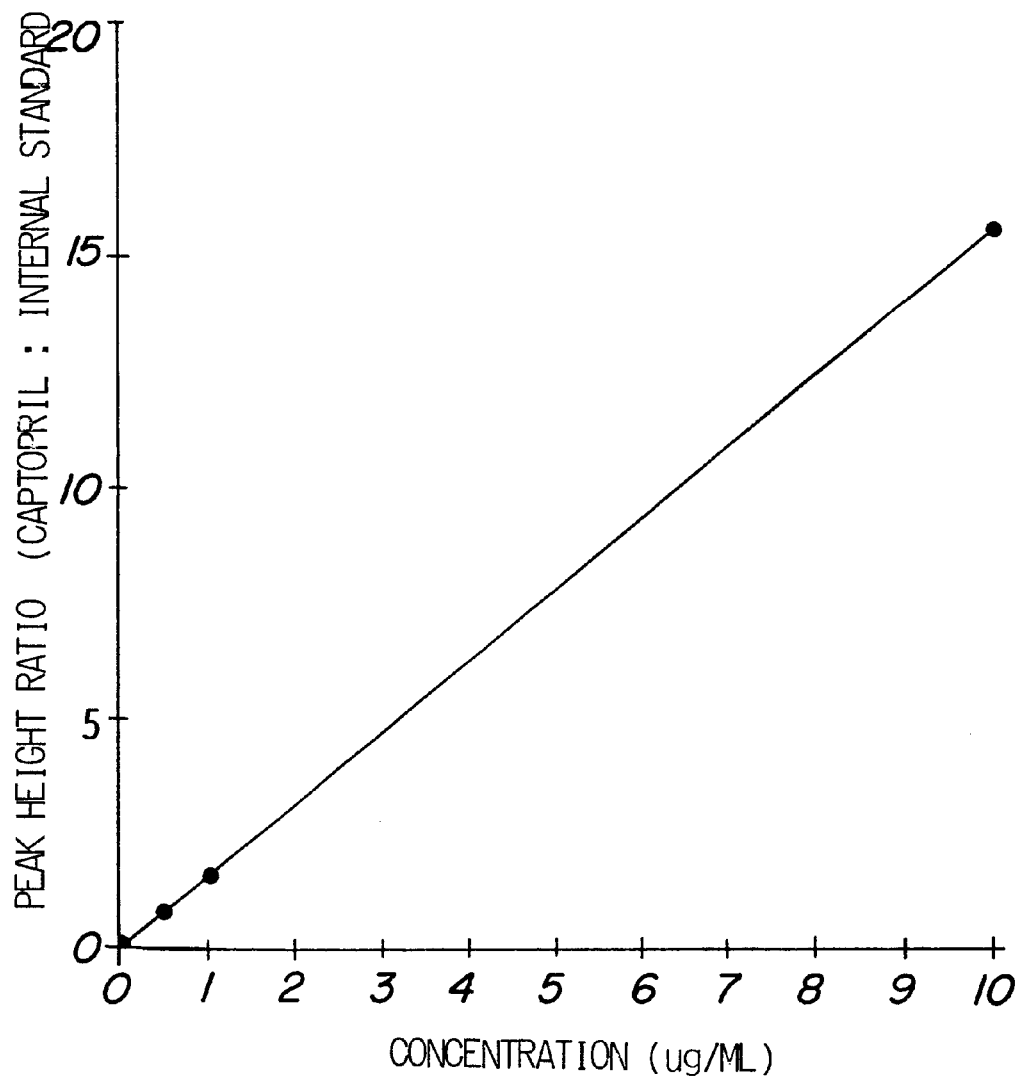
Figure 11A:
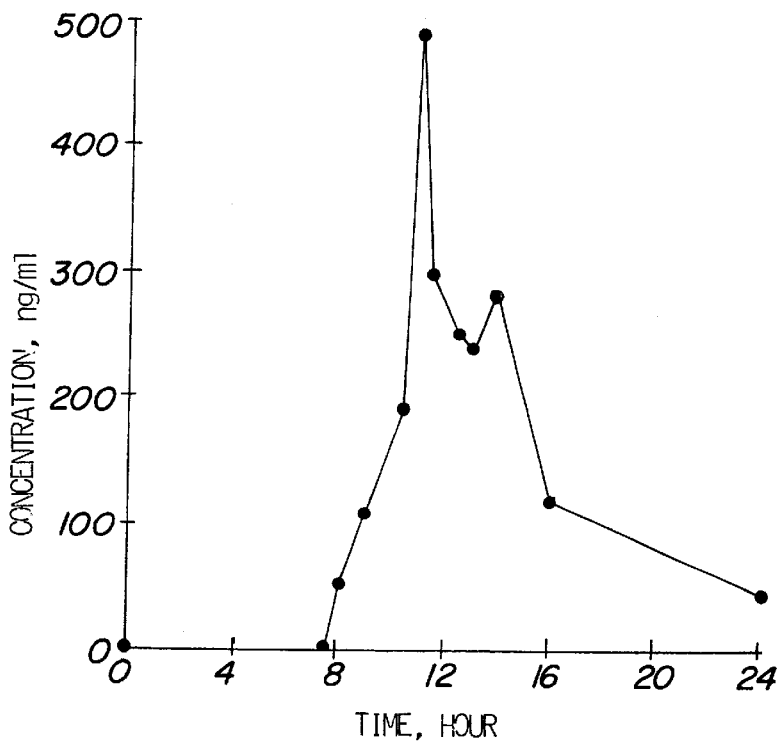
Figure 12:
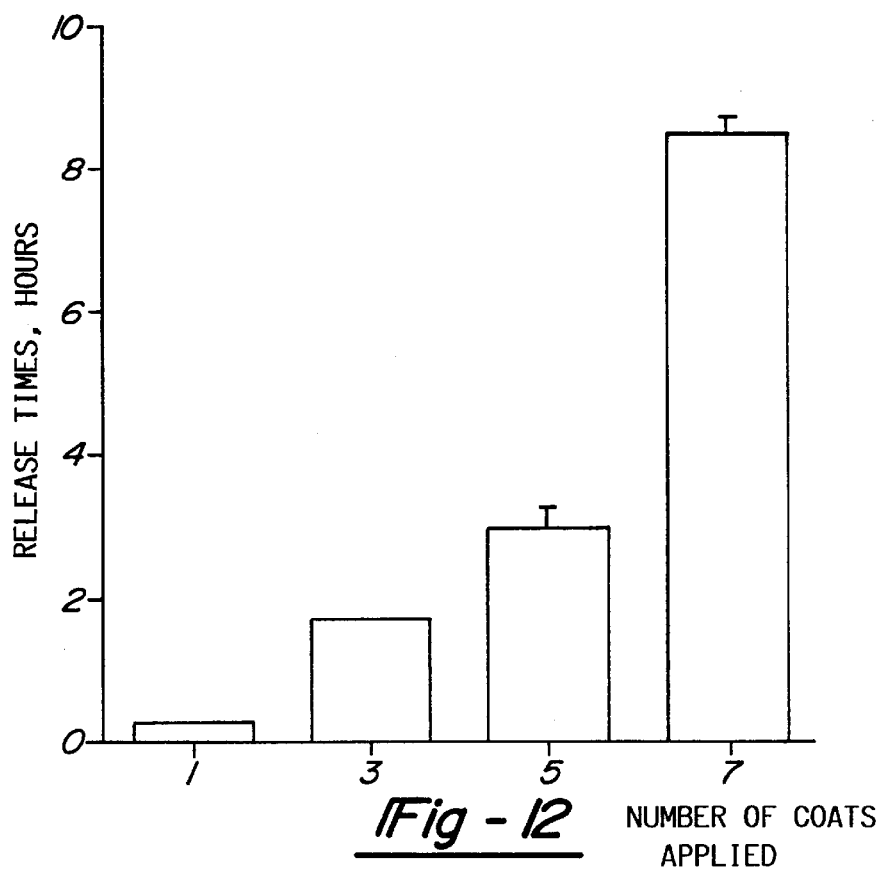
Figure 13:
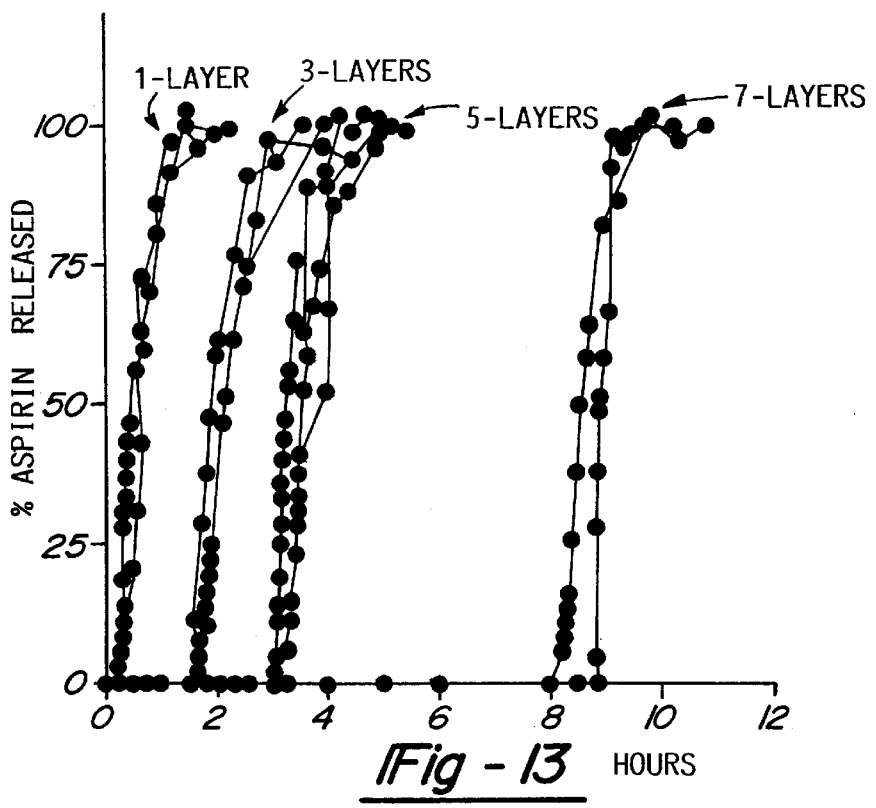

FIG. 3 schematically shows the steps of drug release from the drug delivery system of the present invention over time;

FIG. 4 is a graph showing the percent release of drug from drug delivery systems made in accordance with the present invention over time;

FIG. 5 is a graph showing the average pulse time as function of percent coating;

FIG. 6 shows graphically the results of water uptake studies on capsules made in accordance with the present invention showing percent weight gain over time;

FIG. 7 shows the results of water uptake studies graphically on lactose filled capsules having different coating weights;

FIG. 8 shows the results of water uptake studies of capsules containing lactose/sorbitol therein, the capsules having two different weight coating thereon;

FIGS. 9A and B are chromatograms from blank samples and actual samples from dog studies discussed below;

FIG. 10 shows a plot of chromatographic peak height ratio versus concentration;

FIGS. 11A and B show two graphs illustrating the pulsatile release of drug in vivo;

FIG. 12 is a graph showing the release times of drug as a function of the number of coatings applied to the delivery system; and FIG. 13 is a graph showing the percent release of drug over time as a function of the number of coatings applied to capsules made in accordance with the present invention.

DETAILED DESCRIPTION OF THE INVENTION

A drug delivery system constructed in accordance with the present invention is generally shown at 10 in the Figures. This system generally includes a first container in the form of a capsule half 12 and a second container in the form of a mating capsule half 14. The first capsule half 12 includes an inner chamber 16 for containing a drug 18 therein. Of course, the shape of and size of the capsule half can be varied in accordance with the art.

More specifically referring to FIG. 1A, the first capsule half 12 includes a closed end portion 20 extending to a substantially annular wall 22 defining a second open end 24. The wall 22 and opening 24 define an internal passageway 26 opening to the external environment thereof. A plug 28 is disposed in the passageway 26 for plugging the opening 24 closed. The plug 28 is releasable from the opening 24 upon the application of pressure from within the inner chamber 16. The invention is characterized by the first capsule 12 including a mechanism reactive with the external environment for increasing the pressure within the inner chamber 16 and forcing the plug 28 out of the passageway 26 to release the drug 18 from the inner chamber 16 and out of the passageway 26.

As shown in FIG. 1B, the system can include multiple chambers 16,16' and multiple plugs 28,28'. Each chamber 16,16' includes a mechanism reactive with the external environment for first forcing out plug 28 to release the contents of chamber 16 and then sequentially force out the second plug 28' to release the contents of chamber 16'.

With more specific regard to the reactive mechanism, the reactive mechanism can be a pumping mechanism, such as an osmotic means for pumping fluid through the wall of the first capsule half 12 increasing the internal pressure within the inner chamber 16. Accordingly, once the drug delivery system 10 is ingested at a predetermined time, the reactive mechanism will cause a release of the drug 18 from the first capsule half 16 at predetermined time after ingestion. The rate of internal pressure increase results in the release, timing of the rate being controlled by means described below.

For example, to create the osmotic pump of the present invention, the first capsule half 12 includes a membrane film 30 disposed thereover and over the plug 28 for allowing fluid to pass into the inner chamber 16 as a result of an osmotic pressure gradient therethrough. The osmotic pump further includes an osmotic agent 32 disposed within the inner chamber 16 for creating an osmotic pressure gradient across the membrane film 30 and capsule wall when disposed in the fluid of the external environment.

The open end 34 of the second substantially cupped shaped capsule 14 is seated over and in mating engagement with the open end 24 of the first capsule half 12. The second capsule half 14 includes an inner chamber 36 containing drug 18 therein. The second capsule half 14 is releasably connected to the first capsule half 12 so as to release upon ingestion of the capsule thereby providing an immediate release of drug 18 followed after a predetermined time by the pulse release of the drug 18 from the second capsule half 12.

The capsule halves 12,14 can be made from various materials, preferably water containing gelatins.

The plug 28 can be made from various materials which can, in a plug shape, form a friction fit within the passageway 26 of the first capsule half 12. Plug materials can include bees' wax and synthetic bees' wax, carnauba wax, partial glycerides, polyethylene glycol (PEG), polyglycolized glycerides, fatty acids and/or esters thereof, glyceryl stearate, palmitosterate, paraffin wax, white wax, higher fats, and polymeric materials such as polyurethane, ethylmethacrylate (EMA), hydroxyethylmethacrylate (HEMA).

In the present invention, utilizing a plug 28 preferably made from a viscoelastic polymeric material, such as polyurethane, as an alternative to lipid and wax materials, imparts several advantages to the present invention.

The use of a viscoelastic polymeric material improves the stability of the capsule at temperatures above 60° C. Lipid and wax plug materials typically melt in the temperature range of approximately 35–70° C. Waxes and lipids with higher melting points do not create an effective seal where the plug 28 contacts the internal wall of the capsule half 12 as waxes and lipids with higher melting points constrict upon cooling thereby pulling away from the wall of the capsule half 12 possibly creating an imperfect seal therebetween. Viscoelastic polymers provide constant pressure against the capsule wall at higher temperatures (70–100° C.) thereby perfecting and maintaining a seal therebetween.

The use of viscoelastic polymers to construct the plug 28 additionally improves manufacturing efficiency of the drug delivery system 10 as lipid and wax plug materials must first be melted, then added to the capsule half 12 on top of the powdered drug 18, then the capsule half 12 is sent to a cooling station where the capsule resides for a period of time until the lipid or wax solidifies. A viscoelastic polymer plug 26 can be placed directly into the capsule and the capsule sealed without the cooling step.

A viscoelastic polymer plug 26 can also impart added strength to the capsule half 12. Lipid or wax plug materials can be crushed by squeezing the sealed capsule at the location of the plug 26 and will not return to their original shape. However, a viscoelastic polymer plug 26 can be compressed but will return to its original shape following any deformation of the capsule or plug.

Additionally, the viscoelastic polymer plug can be applied within the capsule half 12 by either directly polymerizing the polymeric material within the capsule half 12 on top of the drug 18 or can be cut or punched from a sheet of polymerized polymeric material and then inserted within the passageway 26 of the capsule half 12 to form a fixation fit within the passageway 26 thereby increasing manufacturing flexibility.

In addition to the drug 18 being disposed within the inner chamber 16, the drug 18 can also be disposed within the plug 28 to use the plug 28 as an effective carrier for an active ingredient or drug 18. The active material can be admixed within the material of which the plug is constructed and then cast into the opening 24 of the capsule half 12 or the drug can be coated onto the plug 28. The feasibility of and utility of adding an active ingredient to the plug 28 is demonstrated below.

Various osmotic agents can be used with the present invention. Agents such as lactose, sorbitol and mannitol can be used. Optionally, the drug contained within the capsule halves 12,14 may also provide sufficient osmotic pressure thereby obviating the need of an additional osmotic agent.

Further the reactive mechanism can be achieved by other agents. For example, swellable gels can be used. Examples of these agents are acrylic acid polymers, hydroxypropyl methyl cellulose, and ethyl cellulose. Alternatively, gas producing agents can be used, such as sodium bicarbonate. It is possible that these agents or additional agents can be added which effect the environment during release. For example, acidifying agents can be added which would acidify a well defined intestinal area where the pulsed dose is released thereby potentiating absorption of the drug without effecting the remainder of the system. Time release systems cannot achieve this localized effect as the agent would be released throughout the tract and substantially diluted.

Various film materials can be used for forming the membrane film 30. Examples of composition for forming the film materials are cellulose acetate (all grades), cellulose acetate butyrate (all grades), cellulose acetate phthalate (all grades), ethylcellulose, polymeric materials such as polyurethane, ethylmethacrylate, and hydroxyethylmethacrylate and combinations of the above.

Table 1 provides a listing of sixty-six drugs which could be used in accordance with the present invention, the list not being an all-inclusive list of such list but rather examples of such drugs.

FIG. 2 schematically illustrates the method of making the drug delivery system 10 in accordance with the present invention. Step A in FIG. 2 shows the first capsule half 12 being empty. Step B shows the capsule half being filled with osmotic reagent 32 and drug 18. As stated above, the drug 18 per se could be the osmotic agent. As shown in Step C, the open end 24 of the first capsule half 12 is plugged with the plug member 28. Step D shows the water permeable film 30 being disposed over the capsule 12 and plug 28. Step D' shows the filling of the second capsule half 14 with the drug 18. Finally, Step E shows the mounting of the open end 34 of the second capsule half 14 over the plugged end 24 of the first capsule half 12.

Of course, many of the steps shown in FIG. 2 can be accomplished by various filling, plugging, and coating methods. For example, Table 2 shows the composition of a preferred captopril containing capsule made in accordance with the present invention. The capsule was made by the following specific method. Also, multi-chambered systems can be made by repeating the filling and coating steps.

Weighed citric acid, anhydrous, USP, was disposed in a mortar and ground thoroughly to a fine powder. Anhydrous lactose, USP, microcrystalline cellulose, NF, sorbitol, NF, Croscarmellos sodium, NF, were added to the mortar containing the citric acid, anhydrous, USP and mixed well. The captopril, USP was added to the mortar containing the excipients of the previous step and mixed thoroughly. The magnesium stearate, BP was added to the mortar and stirred gently. Homogeneity of the mixture was checked from three spots in the mortar taking one gram sample. A 98.4% yield was obtained. A number zero hard gelatin two piece capsule was filled with 350 mg+/−1.5 mg of the fill mix or adjusted to give a potency of 67 mg based on the assay result from the previous step. Utilizing the ingredients set forth in Table 2, a plurality of capsules were filled.

Gelucire 50/02 was melted using a water bath to a constant temperature of 60° C.+/−5° C. 120 mg of the melted gelucire 50/20+/−20 mg was filled into each capsule or five drops of the Gelucire was dispensed using a transfer pipette into each capsule. The capsules were allowed to sit until the gelucire sufficiently solidified. The specific weight (amount) of Gelucire or other plug material can be varied. The capsules were weighed and then placed in a six inch diameter coating pan. Rotation of the coating pan was started and adjusted to a speed of 30 rpm+/−5 rpm. Using a Sigma Glass Spray Unit, the bottle was filled with 225 ml+/−25 ml coating solution. A spray top was fitted on the bottle and tightly capped. A suitable spray pattern was obtained using a compressed air unit by adjusting the air flow and the capsules were sprayed in the pan for sixty seconds. The capsules were allowed to turn in the pan with a stream of compressed air blowing into the pan for sixty seconds. The weight gain of the capsules was calculated as follows:

% gain=coated weight−uncoated weight uncoated weight×100

Thusly, when referring to coating thickness, percent coat is referenced, that meaning the percent gain in weight of the capsule coated by the membrane film. The greater the percent gain, the thicker the coating on the capsule.

To make the final capsules, 66 mg+/−1 mg of the captopril immediate release blend (50%) was disposed into the cap of the size number zero hard gelatin and mounted onto the capsule previously referred to above. The cap was placed on the body taking care not to lose any of the material in the cap or to disrupt the coating on the capsule body. These fine finished capsules were stored in polyethylene bags until tested as described below.

In a preferred embodiment of the present invention, the water permeable film 30 is disposed over the capsule 12 and plug 28 by dipping or immersing the capsule 12 and plug 28 in a reservoir or tank containing the film material. That is, the capsule 12 and plug 28 are immersed in a bath of film material in order to dispose the water permeable film 30 over the capsule 12 and plug 28. The dipping method of the present invention can be performed either prior to filling of the capsule or after the capsule has been filled.

Application of the permeable film 30 by dipping or immersion of the capsule 12 into the film material reduced one of the major problems associated with spray coating which is volatilization of flammable solvents such as acetone. Since spray coating can aerosolize the solvent, it creates a potential for fire or explosion. By immersing the capsule 12 and plug 28 in order to dispose the coating 30 about the capsule 12 and plug 28, much less solvent is aerosolized and, thus, the risk of fire or explosion is reduced. Additionally, since much less solvent is required for dip coating than for spray coating, the dipping or immersion method is much less expensive than spray coating.

The coating material is dissolved in a suitable solvent in order to obtain the desired concentration of the coating to be applied to the capsule 12. Generally, the concentration of the coating material ranges from approximately one to five percent by weight (w/v) of solvent. The preferred range being approximately two to four percent by weight (w/v) of solvent.

Suitable solvents for use in dip coating or immersion coating of the capsules 12 include acetone for water insoluble materials and water ($H_2O$) for water soluble coating materials. Other suitable solvents known to those skilled in the art can also be used.

The capsules 12 are dip coated at approximately room temperature (~20° C.). Following the application of the water permeable film by the dip coating method of the present invention, the coated capsules are dried or "cured" by subjecting the coated capsules to a temperature ranging from approximately 20° C. to 60° C. The preferred drying temperature being approximately 20° C. or room temperature. The coated capsules are subjected to drying temperatures for between one minute to twenty-four hours or until the capsules have reached suitable dryness.

Thickness of the permeable film 30 applied to the capsule can be varied by either increasing/decreasing the number of coats applied or by varying the concentration of the film material to be applied to the capsule 12 and plug 28.

FIG. 4 shows the effective ability of the capsules made in accordance with the present invention to generate a pulse release. First capsule halves 12 made in accordance with the method previously described were tested in vitro for ability to create an osmotic pressure therein to force the release of the plug member 23 and thereby release captopril therefrom. The method consisted of the steps of disposing capsule halves coated as previously described in 28 ml of pH 6.5 buffer solution at 37° C. Samples were initially taken once every hour. At the five hour time period, samples were taken every ten minutes.

A number zero hard gelatin two piece capsule (Capsugel, Greenwood, S. C.) was filled with 200 mg of the osmotic charge (sorbitol/lactose)-aspirin formulation. Gelucire 50/02 was melted using a water bath to a temperature of 50–60° C. The Gelucire 50/20 was added into each capsule or five drops of the Gelucire was dispensed using a transfer pipette into each capsule. The capsules were allowed to sit until the Gelucire sufficiently solidified. The specific weight (amount) of Gelucire or other plug material can be varied. The capsules were weighed and then dip coated (immersed) in an acetone solution containing 0.7% w/v triacetin (Sigma Chemical Co., St. Louis, Mo.) and 2.1% cellulose acetate (FMC Corp., Philadelphia, Pa.). The capsules were allowed to air dry between coats. The weight gain of the capsules was calculated as previously described above. Thusly, when referring to coating thickness, percent coat is referenced, that meaning the percent gain in weight of the capsule coated by the membrane film. The greater the percent gain, the thickener the coating on the capsule.

Capsules having several different numbers of coated layers 30 applied by dipping or immersing the capsule in coating material, as previously described above, were placed in a USP Paddle Dissolution Apparatus (Vankel) containing 900 ml of Simulated Intestinal Fluid, USP (pH 7.5) at 37° C. and rotated at 100 r.p.m. Samples were taken at different time intervals and the total aspirin released at each time point was determined using UV-HPLC and spectrophotometric methods well known in the art. The results of these release studies are illustrated in Table V, FIG. 12, and FIG. 13.

FIG. 12 illustrates the correlation between the number of cellulose film coats and the release time of aspirin in the Simulated Intestinal Fluid at pH 7.5 at 37° C.

FIG. 13 illustrates the percent aspirin released over time as it correlates to the number of cellulose film coatings applied to the capsule subjected to Simulated Intestinal Fluid at pH 7.5 at 37° C.

Table V, FIG. 12, and FIG. 13 demonstrate that the length of release time increases as the number of layers or coatings of cellulose film coatings increased on the dosage form.

As shown in FIG. 4, there is absolutely no release from the capsules during the first 5 hours of testing. There was an immediate pulsatile release from the capsules beginning at five and six hours. Accordingly, capsules made in accordance with the present invention have the capacity to pulse release.

Several variables were evaluated with regard to the manufacturing techniques to determine their effect on pulse time. The results of these tests are shown in Table III.

As shown in Table III, plug variables such as the effect of the hydrophilic/lypophilic balance HLB of the plug on pulse time was tested. The HLB values were varied by varying the components used to make the plug. For example, different waxes have different HLB values. By combining different waxes, the HLB value of the resulting plug is varied. Specific examples are set forth in Table V. Additionally, the temperature of the plug material, such as gelucire, prior to filling also effects pulse time.

Table III also shows the effect of coating variables such as spray rate, solids content and plasticizer content of the coating. What is also evident from Table III is that the variables tested were also effected by the percent coating, that is, the weight percent of the coating as compared to the weight of the remainder of the capsule.

A more detailed analysis of the average pulse time as a function of percent coating is shown in FIG. 5. FIG. 5 shows an almost linear relationship between increased percent coating and pulse time. Thusly, one method of controlling the predetermined time of release is by changing the percent coating of the capsule. As in the prior experiments, this experiment was conducted by coating capsules as described above, determining their percent coating and the placing the capsules as batches based on their percent coating in 20 ml of buffer, 6.5 pH at 37° C. Captopril release was monitored by high pressure liquid chromatography.

Further studies were conducted on the effect of various osmotic agents as they effect water uptake within capsules. To perform these experiments, capsules as made above but filled with lactose, and lactose/sorbitol filled capsules were disposed in 20 ml of buffer, pH 6.5, at 37° C. Six of each capsule type were placed in buffer, the lactose filled capsules and the lactose/sorbitol filled capsules having either a 1.66 weight percent coating or 3.54 weight percent coating. After the periods of time indicated in FIGS. 6–8, the weight of the capsule was determined and percent weight gain was determined as showing comparative rates of the osmotic pressure gradients created by the various agents within the capsules.

FIG. 6 shows an almost linear weight percent gain over time of the Captopril capsules, containing both lactose and sorbitol therein as discussed above. FIG. 7 shows a comparative decrease in weight percent gain over time in the capsules containing only lactose. The expected increase in rate is shown with capsules having the thinner coating of 1.66%. A similar phenomenon is shown with the lactose/sorbitol filled capsules, except that these capsules had a significant increase in rate compared to capsules containing lactose alone.

In view of the above data, the rate of the internal pressure gradient increase and the time period to release the plug member can be adjusted and controlled by adjusting the amount and type of osmotic agent within the capsules, as well as adjusting the thickness of the membrane coating.

The present invention further provides a method of delivering a drug to a body, as schematically shown in FIG. 3. The steps generally include the ingestion of the drug delivery system 10 as shown in FIG. 3. FIG. 3 shows the delivery of the drug over a time, the time line being schematically shown at the bottom of the Figure. There is an initial release of the first predetermined amount of drug 18 from the first chamber 36 of the system 10 after ingestion. The first capsule half 12 remains intact within the membrane 30. As the first capsule half 12 travels through the digestive track it is exposed to the fluid therein, there is a pressure buildup within the inner chamber 16 of the system 10 over time. This forces the plug 28 from the passageway 26 at a predetermined time after the ingesting step. Finally, after the predetermined time, the plug 28 is completely forced from the passageway 26 thereby releasing the drug 18 from the inner chamber 16. A multichamber system works in the same manner with a later pulse of drug 18' being released from chamber 16' and plug 28' is forced out of the capsule half 12. As shown by the in vitro experiments above, the rate of osmotic pressure increase of the inner chamber 16 can be controlled by various variables such as the type and amount of osmotic agent as well as the thickness or percent coating of the membrane film 30.

Applicant has conducted bioavailability studies demonstrating the aforementioned method in vivo.

Materials

Capsules, prepared as described above numbered from 3 to 7, were used for bioavailability study. Captopril tablets and powder for oral and intravenous studies were kindly donated by Squibb. Two male beagle dogs, weighing thirty-four and thirty pounds and two midgut-fistulated female dogs, weighing forty-seven and thirty-eight pounds respectively, were employed for the bioavailability studies. These dogs were fasted over fifteen hours before experiments were began.

Oral study—Four tablets containing 25 mg of Captopril were given to four dogs orally with 20 ml of tap water. Dogs were released from restraining sling for fifteen minutes four hours after the experiment was started for urination and a walk. Blood samples (1.2 ml) were collected through the forearm vein, which was catheterized with an 18G catheter (Abbott, Chicago, Ill.), at 0, 0.25, 0.5, 1, 1.5, 2, 2.5, 3, 3.5, 4, 5, and 6 hours and transferred to test tubes containing 5 mg of each N-ethylmaleimide (NEM) and ethylenediaminetetraacetic acid (EDTA) sodium and stored in a freezer until assay.

Intravenous study—50 mg of captopril powder was dissolved in 15 ml of saline and filtered through 0.22 $\mu$m sterilized filter paper right before the infusion was started. For each four dogs, this solution was infused over fifteen minutes into the catheterized forearm vein using a Harvard infusion pump. For this intravenous study, blood samples were collected from the other side of the forearm vein at 0, 1, 2, 3, 5, 8, 10, 13, 15, 16, 18, 20, 23, 25, 30, and 40 minutes and at 1, 2, 3, and 4 hours.

The study was duplicated in each dog. The experimental design was the same as the oral study except that the schedule for sample collection was every one hour for twelve to thirteen hours. Dogs were released from the sling every four hours for fifteen minutes.

GC-EC blood sample assay—All blood samples were assayed using gas chromatography with an electroncaptured detector. The GC-EC assay, which was reported earlier by Bathala et al., was slightly modified and tested for linearity, precision, and accuracy. The standard curve was linear over the concentration range studied, with an r value of 0.9999. The detection limit based on a signal-to-noise ratio of 3 were 25 ng/ml. The determination of Captopril was highly reproducible, with a CV of less than 7% for all concentrations examined. The intra-and inter-day variability of the Captopril assay was not significant.

Materials—NEM, hexafluoro-2-propanol, trifluoroacetic anhydride, were reagent grade (Sigma Co., Mo.) and used as received. All other chemicals were reagent grade (Fisher Scientific, Chicago) or HPLC grade. Captopril and internal standard, SQ 25761, were obtained from E. R. Squibb & Sons (Princeton). The chromatographic column was capillary, 30 m×0.53 mm i.d. (1.2 mcl of film thickness), immobilized with 100% dimethyl polysiloxane (Cat. #19656, Alltech Assoc., Chicago Ill.). Nitrogen and argonmethane (95:5) of the highest available purity (Metro Welding Co., Detroit, Mich.), were used.

Equipment—Gas chromatography was preformed using HP 5890A (Hewlett Packard) gas chromatograph equipped with a nickel-63 electron-capture detector, 3393A HP integrator, 7673A HP controller, and 7673A HP automatic sampler. All extractions were carried out by shaking the samples on a Tekmar mixer (Janke & Kunkel Co., Funkenstort, West Germany). The N-Evap (Organomation Assoc., Northborough, Mass.) was used to remove benzene from extracts with a nitrogen stream. The esterification with hexafluoro-2-propanol were performed by incubating in a heating block (Lab-Line Instruments Inc., Melrose Park, Ill.).

Blood sample assay—After thawing blood samples by sonication, the blood was diluted with distilled water (1:1 by volume). An internal standard (615 ng/ml) was spiked into blood samples and excess NEM and naturally occurring interfering substances were removed by extraction with benzene followed by acidification and extracted with benzene and converted to their hexafluoroisopropyl esters. These were separated by GC-EC. Standard curves from spiked Captopril concentrations of 0.05. 0.5, 1, 10 mcg/ml in blood were prepared for daily working standards. For reproducibility studies, four concentrations for the standard curve were assayed in quadruplicate using the method described.

Data analysis—Area under curves (AUC) of time zero to t and time zero to infinity by extrapolating the last blood concentration with an elimination rate constant (ke) were evaluated from the oral, intravenous, and technology studies based on the noncompartmental analysis. Relative bioavailability of technology capsules were determined comparing to the oral study and normalized by the dose given.

In view of the experimental results, it can be concluded that capsules made in accordance with the present invention provide a pulsatile release of drugs effective in in vitro environments, as well as in vivo. Such a drug delivery system possess great potential for use in providing drugs to the public that have a first pass effect.

GC-EC assay described above with a slight modification using capillary column, was adequate for the present study. Typical chromatograms from blank blood samples and actual samples from dog studies are shown in FIG. 9A and B respectively. The retention times of the derivatized captopril and internal standard were about 6.2 and 9.6 minutes, respectively. These retention times are different from those reported earlier by Bathala et al. This is probably due to the alteration in instrumentations. No interfering peaks were observed in the extracts of the blank dog blood. The derivatives of captopril and of internal standard were stable over one month (testing period) at room temperature.

A plot of chromatographic peak height ratio versus concentration was linear for captopril from 0.05 to 1 mcg/ml (FIG. 10). The correlation coefficient and the y-intercept for the straight lines were 0.999 and 0.003, respectively. The average coefficient of variation (CV) for all the concentrations examined was +7%. The linearity and reproducibility of the GC-EC method in dog blood by Bathala et al., was demonstrated by 4 consecutive calibration curves in FIG. 2.

Figure 11B:
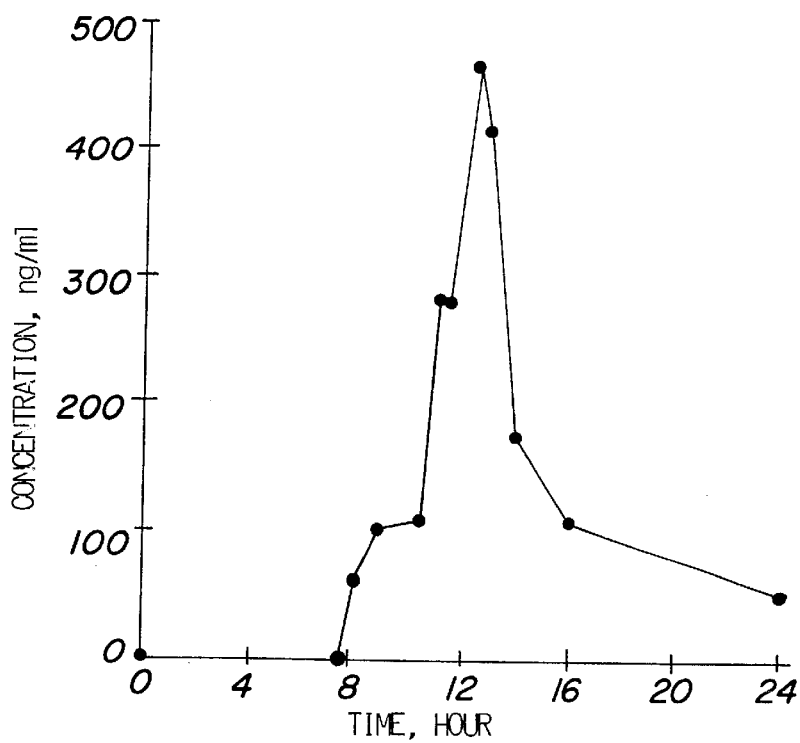

FIGS. 11A and 11B show the results of two dog studies wherein capsules made in accordance with the present invention were ingested. The capsules contained captopril and were made as discussed above. Blood samples were analyzed at the times indicated. There was no release of drug prior to the eight hour time point followed by a pulse or peak of drug. The pulse was a well defined peak. Accordingly, the present invention has been shown to function in vitro as well as in vivo.

POLYMERIC PLUG EXAMPLE

Material and Methods

The polymeric materials were either prepared from monomeric units or purchased synthesized. The polymers were cast into flat sheets, approximately 2–3 mm thick. A circular cutting tool was used to cut disks from the sheets. For the polyurethane plugs, the disks were cut to fit the capsule exactly, for the methacrylic derivatives; the polymeric materials were first hydrated, and then cut slightly larger in size than the capsule opening.

Size 0, hard gelatin capsules were coated with cellulose acetate which was dissolved in acetone and ethanol. Triacetin was used as a plasticizer. The coated capsules were then filled with 340 mg of lactose based placebo powder blend (see Table VI for ingredients), the powder was them tamped into the capsule to a depth of approximately 3–4 mm. Then, the polymeric plugs were placed into the capsules on top of the powder. In the case of the methacrylate derivatives, these hydrogels were first dehydrated so that they fit snugly into the opening.

The filled capsules, constructed as set forth in Table VII, were then placed into simulated intestinal fluid, pH≈7.5, and maintained at 37° C. in a USP Apparatus 2 Dissolution Apparatus with paddles. The paddle speed was set at 100 r.p.m. Wire cages were used to weight the capsules and to hold them on the bottom of dissolution flasks.

Results

Table VII illustrates the plug release times for the polymers tested. Even though the polyurethane plugged capsule had 25% more coating than the ethylmethacrylate (EMA) plugged capsule, the release time for the EMA capsule was longer. This may be due in part to the EMA plug hydrating and forming a tighter union between the plug and the capsule wall. This phenomenon may be advantageous when longer release times are needed and/or when compounded by coating level constraints.

This data clearly demonstrates the utility of polymeric materials for use in forming plugs 26 for use in the present drug delivery system 10.

PREPARATION OF CAPSULES AND RADIOLABELING

Materials and Methods

Caps were removed from size 2 hard gelatin capsules (Capsugel®) and the bodies were manually dipped into a (9% w/v acetone +1.4% w/v triacetin) solution of cellulose acetate (ChemiPharm Capsule Coater) two times with a five minute interval between submersions. The coated capsule bodies were air dried for sixteen hours and were partially filled with 150 mg of an osmotic charge comprised of the following components and mass per each capsule: lactose fast flow (64.5 mg), sorbitol (75.0 mg), sodium starch glycolate (7.5 mg), magnesium stearate (0.75 mg) and samarium hexahydrate (2.25 mg). After filling the capsule bodies with the osmotic charge, a melted mixture of Precirol ATO 5 (Gattefosse') which contained sodium lauryl sulfate and ytterbium oxide was added dropwise on top of the osmotic charge such that each capsule contained approximately 71.1 mg Precirol ATO 5, 5.2 mg ytterbium oxide and 1.1 mg sodium lauryl sulfate. The melted wax hardened at room temperature and the caps were replaced onto the cellulose acetate coated bodies which were now doped with samarium chloride hexahydrate (2.25 mg/capsule) in the osmotic charge and ytterbium oxide (5.2 mg/capsule) in the plug. The two markers, ytterbium and samarium, were chosen because they released different energies and could be distinguished from each other during imaging.

The finished product was completed by neutron activation. The intact capsules were irradiated for fifteen seconds at the Missouri University Research Reactor (Columbia, Mo.) employing a thermal flux of $8\times10^{13}$ neutrons $cm^{-2}/sec^{-1}$. Radioactive doses were received twenty-four hours post activation and were administered approximately forty-eight hours post activation when each capsule contained 12.4 $\mu$Ci samarium-153 and 30.3 $\mu$Ci ytterbium-175.

Human Study

Volunteers reported to the study unit following an eight hour fast and swallowed the radiolabeled capsule under fasted condition or thirty minutes after a standard breakfast. Prior to ingesting the capsule, each subject was fitted with two external markers which facilitated consistent patient positioning in front of the gamma camera.

Immediately after the ingestion of the radiolabeled capsule, subjects were positioned supine beneath the scintillation camera. Subjects were imaged for eight minutes at half hour intervals until it was confirmed that radioactivity had entered the colon and imaging was then performed hourly through eight to twelve hours. A standard lunch was provided after the five hour imaging period and a standard dinner was provided at eleven hours post dose.

Results

Tables VIII and IX show the plug release time based on the gamma scintigraphy for the fed and fasted conditions. Many types sustained release dosage forms incorporate lipids and waxes to delay or sustain the release of drugs embedded within them. Therefore, these data show that the plug can be effectively used as a carrier for an active ingredient whether it is a marker or a pharmaceutically active compound.

POLYMER COATED CAPSULE PREPATATION

Materials and Methods

Size 1 hard gelatin capsules (Capsugel®) were dipped into a solution of 15 gm polyurethane (Spenkel F78-M-50, Reichold) in 30 gm of acetone, USP/NF (Spectrum). This was repeated three more times with 10–15 minutes drying period in between each submersion. During the drying period, warm forced air was used for 2–3 minutes to facilitate drying. The capsules were then filled with 300 mg of an osmotic charge consisting of lactose, sorbitol, magnesium stearate, sodium starch glycolate, and sodium chloride. The powder was tamped into the capsule to a depth of approximately 3 mm. The capsule were then sealed with a melted mixture of Precirol ATO 5 with 1.4% w/w/ sodium lauryl sulfate. When the lipid plugs had hardened, the capsules were again dipped as before into the coating solution×2.

Determination of Release Time

Three flasks of a USP Type 2 dissolution apparatus were filled each with 900 ml of simulated intestinal fluid, USP, pH ≈7.5, and heated and maintained at 37° C.±1° C. The capsules prepared from above were placed into wire baskets and lowered into the dissolution flasks. Paddles were then lowered into the flasks and rotated at 100 rpm. The capsules were periodically observed for plug release. (Plug release was defined as the time at which the plug released from the capsule.) The results are shown in Table X.

Discussion

As is shown in Table X, two capsules released their plug at the same time while one capsule released its plug considerably later. This may have been due to uneven plug depth or coating on the capsule. After the first four coats, each capsule was weighed to determine the amount of coating applied to each capsule. While two of the capsules had coating weights of 30 mg and 35 mg, respectively, one of the capsules had a coating weight of 9 mg. However, since the capsules were coated again after they were filled and this weight was not recorded, the final coating weight is unknown. In any case, there was a significant difference in the amount of coating applied which is the likely contribution to the observed variability in release times.

The above data demonstrates that polyurethane can be used as a coating material for making a multi-stage drug delivery system.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

TABLE I

66 DRUGS WHICH HAVE A FIRST-PASS EFFECT

| | |
|---|---|
| ALDOSTERONE | MEPERIDINE HCL |
| ALPRENOLOL | 6-MERCAPTOPURINE |

TABLE I-continued

66 DRUGS WHICH HAVE A FIRST-PASS EFFECT

| | |
|---|---|
| AMITRYPTYLINE | METAPROTERENOL SULFATE |
| ASPIRIN | METHOXAMINE HCL |
| BECLOMETHASONE DIPROPIONATE | METHYLPREDNISOLONE (F ≅ 0.85) |
| BROMOCRIPTINE MESYLATE (F ≅ 0.06) | METHYLTESTOSTERONE |
| BUTORPHANOL TARTRATE | METOPROLOL TARTRATE |
| CHLORPROMAZINE HCL | MORPHINE SULFATE |
| CIMETIDINE (F ≅ 0.7) | NALBUPHINE HCL |
| CODEINE | NALOXONE HCL |
| CORTISONE | NEOSTIGMINE |
| CYCLOBENZAMINE HCL | NIFEDIPINE |
| DESMETHYLIMIPRAMINE | NITROGLYCERIN |
| DIHYDROERGOTAMINE MESYLATE | NOREPINEPHRINE BITARTRATE |
| DILTIAZEM HCL | NORETHINDRONE (F ≅ 0.65) |
| DOBUTAMINE HCL | NORTRIPTYLENE HCL |
| DOPAMINE HCL | OXPRENOLOL |
| EPINEPHRINE | OXYPHENBUTAZONE |
| ERGOLOID MESYLATES | PENICILLAMINE |
| ERGOTAMINE TARTRATE | PENTAZOCINE HCL & LACTATE |
| ESTRADIOL | PHENACETIN |
| ETHINYLESTRADIOL (F ≅ 0.4) | PHENTOLAMINE HCL & MESYLATE |
| FLUNISOLIDE | PHENYLEPHRINE HCL & BITARTRATE |
| FLUOROURACIL | PREDNISONE (F ≅ 0.85) |
| 5-FLUORO-21-DEOXYURIDINE | PROGESTERONE |
| GUANETHIDINE SULFATE | PROPOXYPHEN HCL & NAPSYLATE |
| HYDRALAZINE HCL | PROPRANOLOL HCL |
| IMIPRAMINE HCL | RITODRINE HCL |
| ISOETHORINE HCL & MESYLATE | SALICYLAMIDE |
| ISOPROTERENOL SULFATE | SALBUTAMOL |
| ISOSORBIDE DINITRATE | TESTOSTERONE |
| LEVALLORPHAN TARTRATE | TIMOLOL MALEATE |
| LIDOCAINE HCL | VERPAMIL HCL |

Source of information was DRUG INFORMATION 84, american Hspital formulary service, american society of hospital pharmacists.

TABLE II

| | |
|---|---|
| Captopril, USP* | 67.00 |
| Citric Acid, Anhydrous, USP | 100.00 |
| Lactose, Anhydrous, USP | 41.00 |
| Microcrystalline Cellulose, NF | 97.35 |
| Sorbitol, NF | 35.00 |
| Croscarmellose Sodium, NF | 7.00 |
| Magnesium Stearate, BP | 1.75 |
| Gelocire 50/02 | 120.00 |
| Size #0 hard gelatin two piece capsules | 66.00 |
| Captopril immediate release blend (50%) | |
| Coating solution for captopril pulsatile release capsules | q.s. to obtain suitable release |

*Microcrystalline cellulose weight to be adjusted based on captopril, USP potency.

TABLE III

Pulsatile Delivery System - variable evaluation:

| Variable | % Coat | Pulse Time | n |
|---|---|---|---|
| Plug Variables: | | | |
| Hydrophilic/Lipophilic Balance (HLB of The Gelucire) | | | |
| 5.5 | 2.80% | 5.00 | 16 |
| 4.0 | 2.75% | 3.95 | 33 |
| 2.0 (current formula) | 2.82% | 6.07 | 12 |
| Temperature of the Gelucire prior to filling | | | |
| 85 C. | 2.78% | 6.52 | 17 |
| 75 C. | 2.82% | 6.07 | 12 |
| 60 C. (current procedure) | 2.85% | 3.42 | 24 |

TABLE III-continued

Pulsatile Delivery System - variable evaluation:

| Variable | % Coat | Pulse Time | n |
|---|---|---|---|
| Coating Variables: | | | |
| Spray Rate | | | |
| Slow (0.038%/appln. | 3.02% | 3.15 | 48 |
| Fast (0.12%/appln. | 2.93% | 4.43 | 43 |
| (Current appln. rate is | 0.080%) | | |
| Solids Content (C. acetate, C. acetate butyrate) | | | |
| 2.8% | 1.0% | 1.07 | 6 |
| | 1.8% | 2.65 | 6 |
| | 2.6% | 3.66 | 6 |
| (Current formula has a 4.2% solids content) | | | |
| Plasticizer | | | |
| 4% PEG 200 | 1.11% | 1.71 | 6 |
| | 1.91% | 3.47 | 6 |
| 0% PEG 200 | 1.13% | 3.01 | 5 |
| (current formula) | 1.46% | 5.04 | 7 |

TABLE IV

| | Plug Material | HLB |
|---|---|---|
| | Examples of mixtures of plug materials to control HLB value | |
| 1. | Partial glycerides and PEG fatty esters | 10 |
| 2. | Partial glycerides and PEG fatty esters | 6 |
| 3. | Glyceryl stearate | 2 |
| 4. | Glyceryl palmitostearate | 2 |

TABLE IV-continued

| | Plug Material | HLB |
|---|---|---|
| | Mixtures of the above materials can be mixed together to achieve Plug materials of varying HLB values. | |
| 5. | 50% Partial glycerides and PEG fatty esters (HLB 10) and 50% Glyceryl stearate | 6 |
| 6. | 50% Partial glycerides and PEG fatty esters (HLB 6) and 50% Glyceryl palmitostearate | 4 |

TABLE V

Release Results

| # of coats applied | % w/w of coat applied | Release Times (hours) |
|---|---|---|
| 1 | 0.18 | 0.23 ± 0.03 |
| 3 | 0.81 | 1.68 ± 0.04 |
| 5 | 1.85 | 2.96 ± 0.31 |
| 7 | 2.90 | 8.53 ± 0.28 |

TABLE VI

Lactose Based Placebo
Lot #1102-5, weight = 193.6 grains, angle of repose of 26°.
Formulation components are as follows:

| | |
|---|---|
| Lactose, #316 Fast-Flow ®, Monohydrate, modified-spray dried, NF Foremost Ingredient Group, Lot #124K427 | 66% |
| Sorbitol, USP/NF Spectrum Chemical, Lot #KE399 | 20% |
| Avicel 101 ®, microcrystalline cellulose, NF FMC, Lot #1903 | 10% |
| Explotab ®, sodium starch glycolate, pH 5.5–7.5, NF Mendell, Lot E5589x | 3.0% |
| Mg Stearate, USP/NF Spectrum Chemical, Lot #HA333 | 0.5% |
| Cab-O-Sil, fumed silica, NF Cabot Corp., Lot #1K305 | 0.5% |

TABLE VII

| Polymer | Amount of Cellulose Acetate Applied to Capsule | Plug Release Time |
|---|---|---|
| Polyurethane | 9 mg | 61 minutes |
| Ethyl Methacrylate (EMA) | 7.2 mg | 80 minutes |
| Hydroxyethyl Methacrylate (HEMA) | 10.6 mg | 146 minutes |

TABLE VIII

Fed Conditions: Subject & Time of Plug Release

| Subject | Time of Release (minutes) |
|---|---|
| 001-BMT | 139 |
| 002-KRF | 137 |
| 003-J G | 108 |
| 004-CER | 169 |
| 005-GJP | 79 |
| 006-JMC | 139 |
| Mean | 129 |
| Standard Deviation | 31 |

TABLE IX

Fasted Conditions: Subject & Time of Plug Release

| Subject | Time of Release (minutes) |
|---|---|
| 001-BMT | 79 |
| 002-KRF | 96 |
| 003-J G | 110 |
| 004-CER | 109 |
| 005-GJP | 139 |
| 006-JMC | 79 |
| Mean | 102 |
| Standard Deviation | 23 |

TABLE X

| Capsule | Release Time, min. | average | standard deviation |
|---|---|---|---|
| #1 | 55 | 78.3 | 40.4 |
| #2 | 55 | | |
| #3 | 125 | | |

What is claimed is:

1. A drug delivery system consisting essentially of: a container (12) defining an inner chamber (16) for containing drug (18) therein and having a passageway (26) opening to an external environment thereof, said container (12) being fluid permeable and a fluid impermeable plug (28) disposed in said passageway (26) for plugging said opening (24) closed, said plug (28) being slidably releasable from said opening (24) upon the application of fluid pressure from within said inner chamber (16) when disposed in a fluid environment and forcing said plug (28) constructed of a viscoelastic polymer to slide out of said passageway (26) to release the drug (18) from said inner chamber (16) and out of said passageway (26).

2. A system as set forth in claim 1, wherein said container (12) includes an osmotic reagent for increasing the pressure within inner chamber (16).

3. A drug delivery system consisting essentially of: a first container (12) defining an inner chamber (16) for containing drug (18) therein and having a passageway (26) opening to an external environment thereof, said container (12) being fluid permeable and a fluid impermeable plug (28) disposed in said passageway (26) for plugging said opening (24) closed, said plug (28) being slidably releasable from said opening (24) upon the application of fluid pressure from within said inner chamber (16) when disposed in a fluid environment and forcing said plug (28) constructed of a material selected from the group consisting of fatty acids and esters thereof, waxes, polyethylene glycol, polyglycolized glycerides, and mixtures thereof to slide out of said passageway (26) to release the drug (18) from said inner chamber (16) and out of said passageway (26).

4. A system of claim 1 containing multiple plugs (28) in the container.

5. A system as set forth in claim 1, wherein said polymer is polyurethane.

6. A system as set forth in claim 1, wherein said polymer is a polymethacrylate.

7. A system as set forth in claim 5, wherein said polymethacrylate is selected from the group consisting of ethylmethacrylate and hydroxyethylmethacrylate.

8. A system as set forth in claim 1, wherein said plug further comprises a drug or active ingredient.

9. A system as set forth in claim 2, wherein said osmotic agent (32) is selected from the group consisting of lactose, sorbitol and mannitol.

10. A system as set forth in claim 1, wherein said inner chamber contains a medicament defining said osmotic reagent.

11. A system as set forth in claim 1 further including a film disposed about said container.

12. A system as set forth in claim 11, wherein said film is a polymer.

13. A system as set forth in claim 12, wherein said polymer is polyurethane.

14. A system as set forth in claim 11, wherein said film comprises a cellulose compound.

15. A system as set forth in claim 14, wherein said cellulose compound disposed over said container is selected from the group consisting of cellulose acetate, cellulose acetate butyrate, ethylcellulose, and cellulose acetate phthalate.

16. A system as set forth in claim 11, wherein the thickness of said film is inversely related to the rate of travel of said plug.

17. A system as set forth in claim 1, further including a swellable agent disposed within said inner chamber (16).

18. A system as set forth in claim 17, wherein said swellable agent is selected from the group consisting of acrylic acid polymers, hydroxypropyl methyl cellulose, and ethyl cellulose.

19. A system as set forth in claim 1, including a reactive agent disposed within said inner chamber capable of causing an increase in internal pressure within said inner chamber.

20. A system as set forth in claim 19, wherein said reactive agent is sodium bicarbonate.

* * * * *